(12) United States Patent
Goossens

(10) Patent No.: US 9,308,770 B2
(45) Date of Patent: Apr. 12, 2016

(54) REFILLABLE RESERVOIR AND FOUNTAIN PEN COMPRISING SUCH RESERVOIR

(71) Applicant: Grocon bvba, Wilrijk (BE)

(72) Inventor: Francis Goossens, St-Niklaas (BE)

(73) Assignee: Grocon bvba, Wilrijk (BE)

( * ) Notice: Subject to any disclaimer, the term of this patent is extended or adjusted under 35 U.S.C. 154(b) by 342 days.

(21) Appl. No.: 13/762,092

(22) Filed: Feb. 7, 2013

(65) Prior Publication Data

US 2013/0209159 A1    Aug. 15, 2013

(30) Foreign Application Priority Data

Feb. 14, 2012    (EP) .................................... 12155412

(51) Int. Cl.
*B43K 5/06*    (2006.01)
*A61M 3/02*    (2006.01)
*A61M 5/315*    (2006.01)

(52) U.S. Cl.
CPC ................ *B43K 5/06* (2013.01); *A61M 3/0262* (2013.01); *A61M 5/31505* (2013.01); *A61M 5/31515* (2013.01)

(58) Field of Classification Search
CPC .... B43K 5/06; B43K 5/1818; A61M 5/31505
USPC ........... 401/176, 182, 251; 403/343, 348, 349
See application file for complete search history.

(56) References Cited

U.S. PATENT DOCUMENTS

| | | | | |
|---|---|---|---|---|
| 566,350 A * | 8/1896 | Stiles | ....................... | B43K 5/06 401/182 |
| 814,805 A * | 3/1906 | De La Rue | ..................... | 401/182 |
| 841,475 A * | 1/1907 | Wirt | ......................... | B43K 5/06 401/182 |
| 863,803 A * | 8/1907 | Luther | ..................... | B43K 5/06 401/174 |
| 1,239,972 A * | 9/1917 | Ruff | ......................... | B43K 5/06 401/182 |
| 1,262,547 A * | 4/1918 | Nedland | ................... | B43K 5/18 401/182 |
| 1,395,878 A * | 11/1921 | Upton | ...................... | B43K 5/06 401/182 |
| 1,445,900 A * | 2/1923 | McKay | .................... | B43K 5/06 401/182 |
| 1,460,386 A * | 7/1923 | Hyman | .................... | B43K 5/06 401/78 |
| 1,464,218 A | 8/1923 | Regero | | |
| 1,509,008 A * | 9/1924 | Wallace | ................... | B43K 5/06 401/182 |
| 1,558,263 A * | 10/1925 | Grommes | ................ | B43K 5/06 401/182 |
| 1,648,241 A * | 11/1927 | Poetz | ...................... | B43K 5/06 401/182 |
| 2,192,644 A * | 3/1940 | La May et al. | ................ | 401/244 |
| 2,557,634 A * | 6/1951 | Eugene | .................... | B43K 5/06 401/182 |
| 5,741,084 A * | 4/1998 | Del Rio | ............ | A61B 17/1633 285/361 |
| 6,270,276 B1 * | 8/2001 | Virgo | ....................... | B43K 5/06 401/181 |

FOREIGN PATENT DOCUMENTS

FR        888 803        12/1943

* cited by examiner

*Primary Examiner* — David Walczak
*Assistant Examiner* — Bradley Oliver
(74) *Attorney, Agent, or Firm* — Levy & Grandinetti

(57) ABSTRACT

The invention is a reservoir having a piston assembly for filing and/or dispensing fluids contained in the reservoir. The refillable reservoir includes a cylinder defining a reservoir for containing a fluid; a piston body axially slidable in the reservoir; and a piston rod releasably fixed to the piston body for actuating the piston body. A first locking mechanism is provided between the piston body and the cylinder. A second locking mechanism is provided between the piston body and the piston rod.

18 Claims, 4 Drawing Sheets

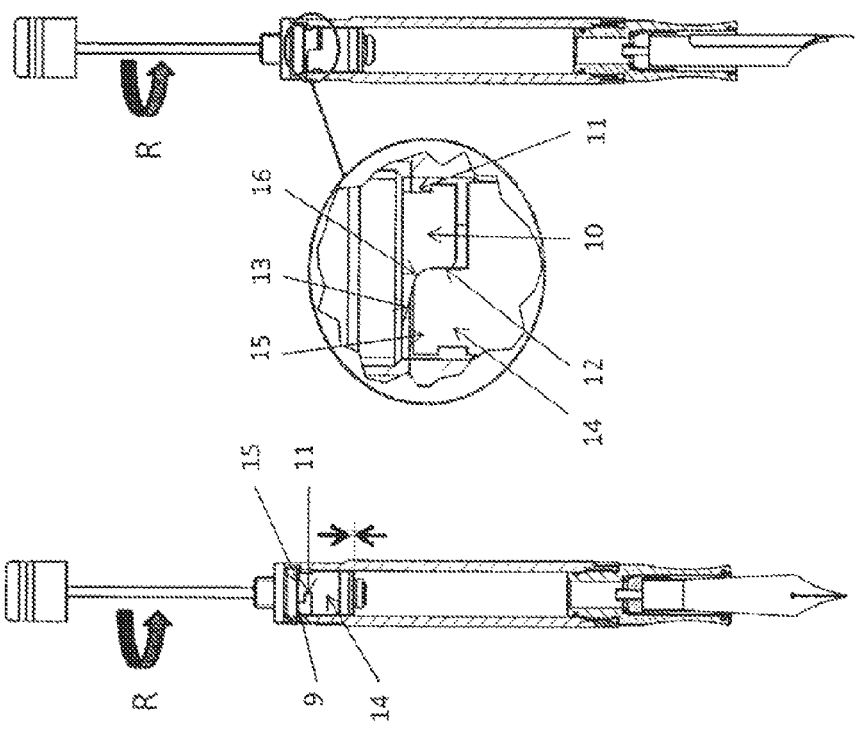

REFILLABLE RESERVOIR AND FOUNTAIN PEN COMPRISING SUCH RESERVOIR

This Application claims priority to European Application Number EP12155412 filed on Feb. 14, 2012.

FIELD OF THE INVENTION

The present invention concerns a refillable reservoir comprising a piston assembly for filling and/or dispensing fluids contained in the reservoir, said refillable reservoir comprising:
  (a) a cylinder defining a reservoir for containing a fluid;
  (b) a piston body axially slideable in said reservoir;
  (c) a piston rod releasably fixed to the piston body for actuating the piston body

BACKGROUND OF THE INVENTION

In current times where computers and tablet computers are increasingly important for writing, handwriting too is becoming a more niche market with increasing demands, especially regarding fountain pens. One of the most important advantages of handwriting versus computers or such is the high autonomy and independence of electricity.

Fountain pens have an internal ink reservoir that can be filled in various manners. Early fountain pens for example used an eyedropper system wherein the nib unit had to be removed from the reservoir for refill. Such filling systems however are conceived as messy, time consuming and hence impractical.

Other fountain pens are provided with a piston movable to-and-fro the cylinder reservoir for refilling the pen through the pen nib. The piston can be actuated by a piston rod fixedly attached to the piston body and protruding through the distal end of the cylinder. This construction has the disadvantage that when the reservoir is filled the piston rod projects a substantial axial distance beyond the distal end of the cylinder. As a consequence the piston mechanism takes up a relatively large portion of the space available in the pen barrel and therefore restricts the maximum length of the cylinder and hence the volume of the Ink chamber within it and the autonomy of the pen.

U.S. Pat. No. 6,270,276 addresses the above problem and as a solution provides a fountain pen with a refillable cylinder reservoir wherein a piston body is slideably accommodated and is actuated by a rod that is releasably fixed to the piston body and extends through a channel in said piston body. In order to actuate the piston body, the piston rod is retreated from the cylinder until the frontal end of the piston rod contacts the piston body and is fixed thereto by means of a screw thread connection. Once fixed the piston body can be pushed to-and-fro in the cylinder to fill or refill the cylinder. After refill, the piston rod is unscrewed from the piston body and pushed into the cylinder. As such nearly the entire shaft of the pen can be used as ink reservoir, thereby considerably increasing the pen's autonomy.

An inconvenience of a fountain pen as disclosed in U.S. Pat. No. 6,270,276 is that when the piston body is not actuated for a while, slip-stick phenomena occur inhibiting gently pushing the piston body to the frontal end of the reservoir. As a relatively large force is needed to overcome the slip-stick phenomena, the piston body will be pushed forward with high speed and air and ink present in the reservoir will be pushed out suddenly and in an uncontrolled manner leading to spilling.

Furthermore, when after filling, the piston rod is to be unscrewed from the piston body, rotation of the piston body in the cylinder will prevent such unscrewing and urge the user to exert a radial force on the piston rod to block the piston body in the cylinder to allow unscrewing, however at the cost of potentially damaging the fountain pen.

From the above it is clear that there remains a need for providing n easy to use fountain pen with a large autonomy.

BRIEF DESCRIPTION OF THE INVENTION

The current invention addresses the above mentioned problems and concerns a refillable reservoir comprising a piston assembly for filling and/or dispensing fluids contained in the reservoir, said refillable reservoir comprising:
  (a) a cylinder defining a reservoir for containing a fluid;
  (b) a piston body axially slideable in said reservoir;
  (c) a piston rod releasably fixed to the piston body for actuating the piston body, said wherein (i) a first locking mechanism is provided between the piston body and the cylinder; and wherein (ii) a second locking mechanism is provided between the piston body and the piston rod.

The present invention also concerns a fountain pen comprising a reservoir as described here above.

Syringes or foam applicators comprising a reservoir as described above are also envisaged by the present invention.

SUMMARY OF THE INVENTION

The first locking mechanism preferably comprises means preventing rotation of the piston body around an axial axis of the cylinder in a first direction when in a locked position, while the second locking mechanism locks the piston rod in view of the piston body against rotation in a second direction, opposite to said first direction.

It is preferred that the first locking mechanism comprises means preventing axial displacement of the piston body when in a locked position.

According to a preferred embodiment of the present invention, the first locking mechanism is provided between a distal end of the piston body and a distal end of the cylinder. Said first locking mechanism may comprise a slot provided on the cylinder and a hook provided on the piston body or vice versa.

It is highly preferred that a wedge is provided between the piston body and the cylinder, wherein the wedge is oriented axially in view of the cylinder such as to force the piston body to move axially when releasing the first locking mechanism.

The piston body preferably comprises a axial opening whereby the piston rod slideably extends through said opening.

The piston rod is preferably provided with a actuating knob at its distal end, and wherein third locking means are provided between the actuating knob and the cylinder.

BRIEF DESCRIPTION OF THE DRAWINGS

FIGS. 1-8 represents a fountain pen according to the present invention in vane positions of piston body and piston rod.

DETAILED DESCRIPTION OF THE INVENTION

Figure 8:
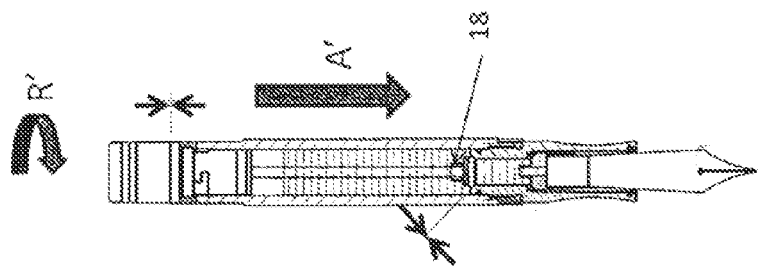

FIG. 1 represents a fountain pen 1 according to the present invention comprising a barrel in the form of a cylinder 2 defining an ink reservoir 3. A head section 4 defining a pen feed for connection with a nib 5 is sealingly fitted in the frontal end of the cylinder 2 and has a central port 6 communicating with the ink reservoir 3.

Slidable axially within the cylinder 2 is an annular piston body 7 that is provided with an axial opening, where through a piston rod 8 is provided that projects through the distal end of the cylinder 2 and carries a knob 9 on its outer end.

As represented in FIG. 3, inner surface of the cylinder at its distal end is provided with a rim 10 extending along a section of the circumferential edge of said surface. Said rim comprises a cutout portion defining a transversal slot 11 at one of its transversal edges and an abutment surface 12 at its opposite edge extending into a wedge portion 13 provided in the inner surface of the distal end of the cylinder and increasing towards the abutment surface of the rim 10.

The distal surface of the piston body 7 is also provided with a rim 14 comprising a cutout portion defining a hook 15 oriented such that it can cooperate with the transversal slot 11 on the opposed cylinder surface to lock the piston body in view of the cylinder against both axial displacement and rotation in a direction R, preferably a clockwise rotation. At the opposite edge of rim 14 is defined as an abutment surface 16.

The piston rod 7, conveniently formed from a metal rod, has a coupling member 17, secured to its frontal end, this member comprising a screw-threaded section 18 and an enlarged head 19 having dimensions larger than the cross-section of the opening in the piston body 7. The piston body has an internal screw-threaded bore for cooperation with the coupling member 17 of the piston rod, and the piston carries seals against both the cylinder 2 and the piston rod 8. The cooperating screw-threads of the piston body and piston rod preferably mate in a direction R' opposite to the above mentioned direction R for locking the piston body in view of the cylinder 2.

The enlarged head 19 of the piston rod is preferably provided with a seal 21 allowing sealing the central port 6 of the above mentioned connection part 4 of the pen 1.

Finally, the outer surface of the cylinders' distal end is provided with a protruding screw-threaded portion cooperating with a inner screw-thread in the knob 9 provided on the piston rod 7. These screw threads are preferably oriented to allow locking the knob on the cylinder by a rotation in direction R.

Handling and especially refilling of the pen is easy and user friendly as will be apparent from the below description.

Starting from a situation wherein the pen is empty and needs to be refilled. In this position, the piston body 7 is locked in view of the cylinder 2 by means of a first locking mechanism comprising the above mentioned hook 15 and slot 11 at the opposing surfaces of the piston body and cylinder 2. Further the piston rod 8 is loose from the piston body and inserted nearly entirely into the cylinder, whereby the knob 9 is screwed onto the cylinder.

FIG. 1 represents a first step wherein the knob 9 is unscrewed from the cylinder and the rod is subsequently pulled out of the cylinder 2, until the screw-threaded portions of the second locking mechanism (locking between the rod and the piston body) engage. At this point and as represented in FIG. 2, the piston rod is rotated in a direction R' to lock the piston rod's connection member 10 in the piston body 7 allowing actuation of the piston body by the rod. Once the second locking mechanism is in a locked position, rotation of the piston rod in a direction R' is continued thereby retreating the hook 15 of the piston body from the slot 11 on the cylinder such that the piston body is unlocked from the cylinder. As represented in FIG. 3, this rotation will force the rim 14 of the piston body to slide along wedge 13 thereby displacing the piston body in a axial direction A' in the cylinder. This axial displacement powered by rotation of the piston body 7 is important to gently overcome any slip-stick phenomena occurring between the piston body and the cylinder and guarantees that a smooth and controlled further displacement of the piston body in the cylinder is possible by axial displacement of the piston rod as represented in FIG. 4.

Figure 6:
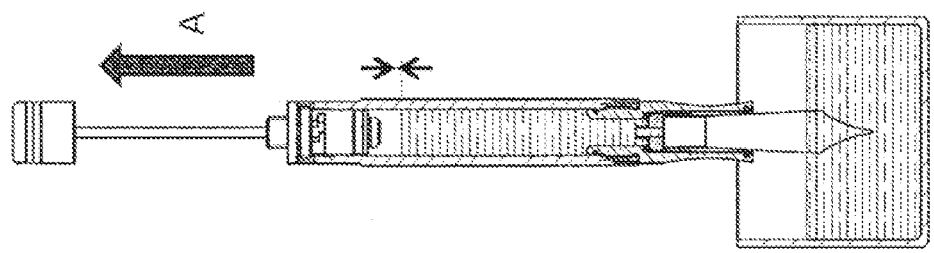
Figure 5:
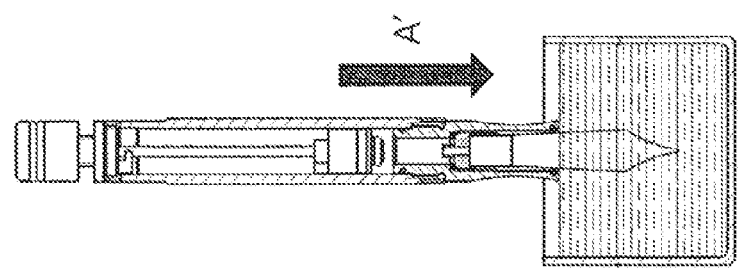

Moving the piston body 7 towards the frontal end of the cylinder 2 will drive all air out of the ink reservoir. By subsequently placing the nib of the pen in a ink pot (FIG. 5) and retraction of the piston rod 8 from the cylinder in a direction A, ink is sucked into the reservoir 3 as represented in FIG. 6.

Figure 7:
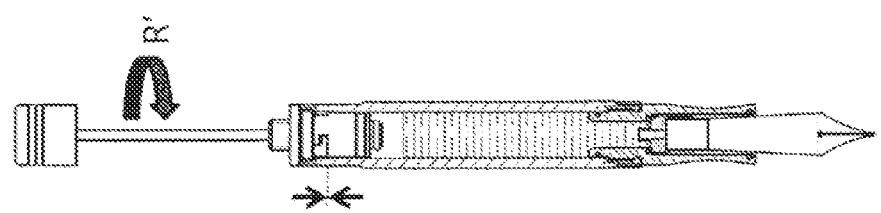

Once the piston rod 8 is maximally retracted from the cylinder 2, the piston body 7 contacts the distal end of the cylinder and can be locked to the cylinder 2 by rotation of the rod and hence piston body in a direction R (FIG. 7). Once the piston body is locked further rotation of the piston rod 8 in the direction R will incur unscrewing of the piston rod from the piston body that can subsequently be pushed into the cylinder again and can be fixed by locking the knob 9 on the cylinder by screwing. The length of the rod 8 is chosen such that when the knob is entirely screwed onto the cylinder, the seal 21 at the head of the piston rod seals the central port 6 at the frontal end of the ink reservoir 3 (FIG. 8) such that the pen can be stored without the risk of ink spoiling from the reservoir.

In order to write with the pen, the knob 9 is partially unscrewed from the cylinder over a distance of for example 1 mm, such that the seal 21 of the piston rod's head is disconnected from the central port and ink can flow from the reservoir 3 to the nib 5

It is clear that the first and second locking mechanisms can be executed in various alternatives such as a bayonet lock or a screw-threaded lock. It is however preferred that the force necessary for locking the first locking mechanism is smaller than the force needed to unlock the second locking mechanism to ensure that the piston rod is not disconnected from the piston body 7 as long as the piston body is not locked to the cylinder 2.

Figure 11:
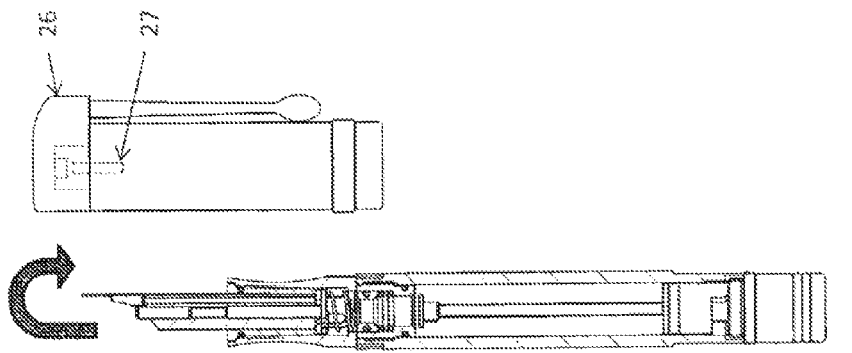
FIGS. 9-11 represent an alternative fountain pen according to the present invention.
Figure 10:
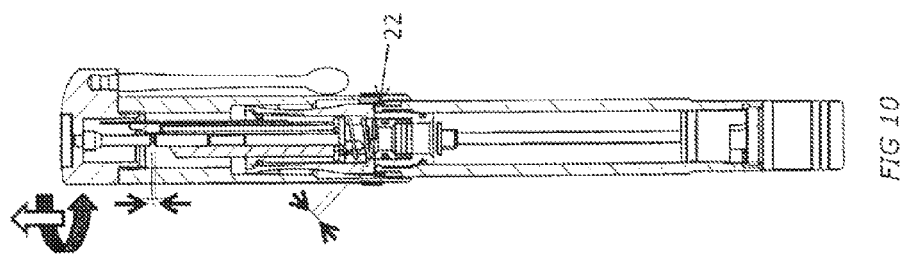
Figure 9:
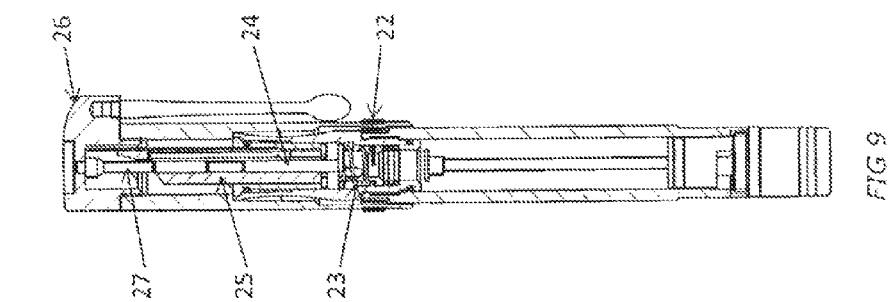

As an alternative to the sealing of the ink reservoir by the head 19 of the piston rod 8 against the central port 6, FIGS. 9-11 show an embodiment wherein a valve 22 is provided inside the head section 4 frontal from the central port 6.

This valve is preferably a spring-actuated valve actuated by a rod 24 provided slideably into a channel 25 through a fountain pen feed. The channel is preferably straight and most preferably provided centrally in the fountain pen feed.

In order to move and maintain the rod 24 pushing the valve against the spring force in a closed position, the pen 1 is provided with a cap 26 provided with a actuating pin 27 projecting internally and cooperating with the rod 24 when fixing the cap 26 on the pen.

This alternative embodiment has the advantage that the ink reservoir is automatically shut-off when the cap is placed on the pen 1, without the need to turn the knob 9 back in to a closed position after writing. This improves user friendliness and diminishes accidental leaking of the pen 1, especially due to changes in ambient pressure such as during airplane or mountain travelling.

Figure 13:
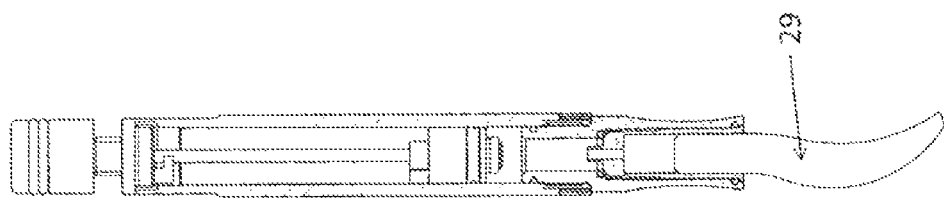
FIGS. 12-13 respectively represent a syringe and foam applicator according to the present invention.
Figure 12:
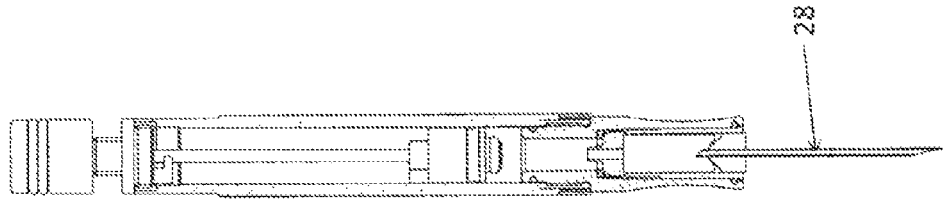

In the above description the refillable reservoir according to the present invention has been described in an embodiment of a fountain pen, however it is clear that the reservoir according to the present invention can also be applied for syringes 28 or foam applicators 29 as represented in FIGS. 12 and 13, respectively.

The invention claimed is:

1. A refillable reservoir comprising:
   (a) a cylinder defining a reservoir for containing a fluid;
   (b) a piston body axially slidable in said reservoir; and
   (c) a piston rod releasably fixed to the piston body for actuating the piston body, the refillable reservoir further comprising:
   a first locking mechanism provided between the piston body and the cylinder;
   a second locking mechanism provided between the piston body and the piston rod, and
   a wedge fixed on said cylinder between the piston body and the cylinder, wherein the wedge is oriented axially in view of the cylinder such as to force the piston body to move axially when releasing the first locking mechanism.

2. The refillable reservoir according to claim 1, wherein the first locking mechanism comprises a first lock preventing rotation of the piston body around an axial axis of the cylinder in a first direction when in a locked position.

3. The refillable reservoir according to claim 2, wherein the first locking mechanism comprises a second lock preventing axial displacement of the piston body when in a locked position.

4. The refillable reservoir according to claim 1, wherein the first locking mechanism is provided between a distal end of the piston body and a distal end of the cylinder.

5. The refillable reservoir according to claim 3, wherein the first locking mechanism comprises a slot provided on the cylinder and a hook provided on the piston body or vice versa.

6. The refillable reservoir according to claim 2, wherein the second locking mechanism locks the piston rod in view of the piston body against rotation in a second direction, opposite to said first direction.

7. The refillable reservoir according to claim 1, wherein the piston body comprises a through opening whereby the piston rod slidably extends through said opening.

8. The refillable reservoir according to claim 7, wherein the piston rod is provided with an actuating knob at its distal end, and wherein a third lock is provided between the actuating knob and the cylinder.

9. A refillable reservoir according to claim 1 further comprising a fountain pen.

10. A refillable reservoir according to claim 1 further comprising a syringe.

11. A refillable reservoir according to claim 1 further comprising a foam applicator.

12. The refillable reservoir according to claim 1, wherein the first locking mechanism comprises means preventing axial displacement of the piston body when in a locked position.

13. The refillable reservoir according to claim 1 wherein the first locking mechanism comprises a slot provided on the cylinder and a hook provided on the piston body or vice versa.

14. The refillable reservoir according to claim 2 wherein the first locking mechanism comprises a slot provided on the cylinder and a hook provided on the piston body or vice versa.

15. The refillable reservoir according to claim 4 wherein the first locking mechanism comprises a slot provided on the cylinder and a hook provided on the piston body or vice versa.

16. The refillable reservoir according to claim 9, wherein the first locking mechanism comprises means preventing rotation of the piston body around an axial axis of the cylinder in a first direction when in a locked position.

17. The refillable reservoir according to claim 16, wherein the first locking mechanism comprises means preventing axial displacement of the piston body when in a locked position.

18. The refillable reservoir according to claim 17, wherein the first locking mechanism comprises a slot provided on the cylinder and a hook provided on the piston body or vice versa.

* * * * *